(12) United States Patent
Hashiguchi

(10) Patent No.: US 9,993,138 B2
(45) Date of Patent: Jun. 12, 2018

(54) RIGID ENDOSCOPE SET

(71) Applicant: OLYMPUS CORPORATION, Tokyo (JP)

(72) Inventor: Toshihiko Hashiguchi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/273,838

(22) Filed: Sep. 23, 2016

(65) Prior Publication Data

US 2017/0007103 A1 Jan. 12, 2017

Related U.S. Application Data

(63) Continuation of application No. PCT/JP2015/061344, filed on Apr. 13, 2015.

(30) Foreign Application Priority Data

Aug. 21, 2014 (JP) .................................. 2014-168622

(51) Int. Cl.
*A61B 1/00* (2006.01)
*A61B 8/12* (2006.01)
(Continued)

(52) U.S. Cl.
CPC .......... *A61B 1/00147* (2013.01); *A61B 1/015* (2013.01); *A61B 1/018* (2013.01);
(Continued)

(58) Field of Classification Search
CPC .... A61B 1/00098; A61B 1/0125; A61B 1/018
(Continued)

(56) References Cited

U.S. PATENT DOCUMENTS 1,969,342 A * 8/1934 Wappler ................. A61B 1/018
600/104
4,436,087 A * 3/1984 Ouchi .................. A61B 1/0008
600/106
(Continued)

FOREIGN PATENT DOCUMENTS

EP 1 872 708 A1 1/2008
EP 2671513 A1 12/2013
(Continued)

OTHER PUBLICATIONS

International Search Report dated Jun. 23, 2015 issued in PCT/JP2015/061344.
(Continued)

*Primary Examiner* — Matthew J Kasztejna
(74) *Attorney, Agent, or Firm* — Scully, Scott, Murphy & Presser, P.C.

(57) ABSTRACT

A rigid endoscope set according to the invention includes a rigid endoscope body having a first insertion portion inserted into a subject, a first channel provided in the first insertion portion and an ultrasound observation section disposed at a distal end of the first insertion portion to observe the subject, a treatment instrument guide having a second insertion portion configured to be inserted into or removed from the first channel and a second channel provided in the second insertion portion, and an optical telescope having a needle portion configured to be insertable into or removable from the second channel, a third insertion portion configured to be insertable into or removable from the first channel instead of the treatment instrument guide and an optical observation section disposed at a distal end of the third insertion portion to observe the subject.

11 Claims, 11 Drawing Sheets

(51) Int. Cl.
  *A61B 1/015* (2006.01)
  *A61B 1/018* (2006.01)
  *A61B 1/04* (2006.01)
  *A61B 1/06* (2006.01)
  *A61B 1/307* (2006.01)
  *A61B 1/012* (2006.01)

(52) U.S. Cl.
  CPC .............. *A61B 1/0125* (2013.01); *A61B 1/04* (2013.01); *A61B 1/06* (2013.01); *A61B 1/307* (2013.01); *A61B 8/12* (2013.01); *A61B 1/00098* (2013.01); *A61B 1/012* (2013.01)

(58) Field of Classification Search
  USPC .................. 600/105–107, 121–125, 137
  See application file for complete search history.

(56) References Cited

U.S. PATENT DOCUMENTS

| | | | | |
|---|---|---|---|---|
| 4,763,662 | A * | 8/1988 | Yokoi | A61B 1/015 600/101 |
| 5,386,817 | A * | 2/1995 | Jones | A61B 1/00091 138/108 |
| 5,820,546 | A * | 10/1998 | Ouchi | A61M 25/0662 600/104 |
| 5,836,951 | A * | 11/1998 | Rosenbluth | A61F 2/958 600/116 |
| 5,873,828 | A * | 2/1999 | Fujio | A61B 1/0051 600/439 |
| 5,931,787 | A * | 8/1999 | Dietz | A61B 8/0833 600/461 |
| 6,210,378 | B1 * | 4/2001 | Ouchi | A61M 25/0068 600/154 |
| 6,302,875 | B1 * | 10/2001 | Makower | A61B 8/12 604/528 |
| 6,352,503 | B1 * | 3/2002 | Matsui | A61B 1/00071 600/104 |
| 6,368,280 | B1 | 4/2002 | Cermak et al. | |
| 7,811,265 | B2 * | 10/2010 | Hering | A61B 8/12 600/407 |
| 9,149,602 | B2 * | 10/2015 | Chow | A61M 25/003 |
| 2001/0056222 | A1 * | 12/2001 | Rudischhauser | A61B 1/00135 600/130 |
| 2007/0038089 | A1 * | 2/2007 | Hatano | A61B 8/0833 600/437 |
| 2007/0066869 | A1 * | 3/2007 | Hoffman | A61B 1/00135 600/121 |
| 2007/0249939 | A1 * | 10/2007 | Gerbi | A61B 8/0833 600/462 |
| 2009/0270812 | A1 * | 10/2009 | Litscher | A61B 1/303 604/164.01 |
| 2012/0078094 | A1 | 3/2012 | Nishina et al. | |
| 2013/0225995 | A1 | 8/2013 | Hashiguchi et al. | |

FOREIGN PATENT DOCUMENTS

| | | |
|---|---|---|
| JP | H01-284234 A | 11/1989 |
| JP | 2000-139927 A | 5/2000 |
| JP | 2002-263062 A | 9/2002 |
| JP | 3514854 B2 | 3/2004 |
| WO | WO 2013/062039 A1 | 5/2013 |
| WO | 2014/013491 A1 | 1/2014 |

OTHER PUBLICATIONS

Japanese Office Action dated Apr. 5, 2016 issued in JP 2015-553977.

Extended Supplementary European Search Report dated Oct. 27, 2017 received in 15834119.8.

\* cited by examiner

RIGID ENDOSCOPE SET

CROSS REFERENCE TO RELATED APPLICATION

This application is a continuation application of PCT/JP2015/061344 filed on Apr. 13, 2015 and claims benefit of Japanese Application No. 2014-168622 filed in Japan on Aug. 21, 2014, the entire contents of which are incorporated herein by this reference.

BACKGROUND OF INVENTION

1. Field of the Invention

The present invention relates to a rigid endoscope set in which a third insertion portion provided in a telescope is allowed to be inserted into or removed from a first channel of a rigid endoscope body and a treatment instrument having a smaller outer diameter than that of the third insertion portion is allowed to be inserted into or removed from the first channel with assistance of a treatment instrument guide.

2. Description of the Related Art

Diagnosis or treatment on a patient using a rigid endoscope body is generally performed under observation using an optical endoscope or an ultrasound endoscope or the like. With a rigid endoscope body provided with optical observation means at a distal end, the distal end of the rigid endoscope is guided to a target subject based on an optical observation image acquired from the optical observation means, a tissue is extracted using a treatment instrument inserted into a channel of the rigid endoscope body or necessary treatment is performed.

For example, Japanese Patent No. 3514854 discloses a technique of performing diagnosis and/or treatment on a subject using an ultrasound probe provided with a flexible or rigid insertion portion, provided with ultrasound observation means, optical observation means and a channel opening arranged at a distal end.

When performing diagnosis or treatment on a subject using the ultrasound probe disclosed in Patent Literature 1, the insertion portion of the ultrasound probe is inserted into the body first and the distal end of the ultrasound probe is guided into the subject based on an optical observation image acquired from the optical observation means. Next, the ultrasound observation means is brought into contact with the subject, a lesioned region is identified and predetermined treatment is performed. Furthermore, a treatment instrument is inserted into a channel provided in the ultrasound probe and other treatment is performed.

Note that when transluminally performing diagnosis or treatment on a target subject, particularly when the insertion portion of the rigid endoscope body such as an ultrasound probe is inserted into a relatively narrow luminal such as urethra, the outer diameter of the insertion portion of the rigid endoscope body is preferably as small as possible to alleviate the burden on patients.

The outer diameter of the insertion portion can be reduced by separating the optical observation means from the rigid endoscope body, inserting the optical observation means into the channel provided in the rigid endoscope body as an optical telescope and guiding the distal end portion to a target tissue according to an observed image acquired from the optical telescope.

SUMMARY OF THE INVENTION

A rigid endoscope set according to an aspect of the present invention includes a rigid endoscope body having a first insertion portion inserted into a subject configured to include an elongated longitudinal axis, a first channel provided in the first insertion portion and an ultrasound observation section disposed at a distal end of the first insertion portion to observe the subject, a treatment instrument guide having a second insertion portion configured to be insertable into or removable from the first channel and formed to have an outer diameter adaptable to the first channel and a second channel formed of a resin material filling an interior of the second insertion portion so as to be decentered with respect to the axis of the second insertion portion, a treatment instrument configured to be insertable into or removable from the second channel, an imaging device having a third insertion portion formed to be insertable/removable into/from the first channel with an outer diameter adaptable to the first channel instead of the treatment instrument guide and an optical observation section disposed at a distal end of the third insertion portion to observe the subject, and a positioning mechanism configured to fix, when the imaging device is inserted into the first channel, the rigid endoscope body and the imaging device in a state in which a minute gap is secured to circulate a perfusate between the first channel and the third insertion portion, fix the imaging device to restrict the imaging device from moving in the turning direction of the longitudinal axis of the rigid endoscope body, and fix, when the treatment instrument guide is inserted into the first channel, the treatment instrument guide to the rigid endoscope body by causing the axis center of the second channel to decenter so that the treatment instrument projects in a direction in which the treatment instrument moves away from the ultrasound observation section.

DETAILED DESCRIPTION OF THE PREFERRED EMBODIMENT(S)

Hereinafter, an embodiment of the present invention will be described with reference to the accompanying drawings. Note that the drawings are schematic ones, and a relationship between a thickness and a width of each member, a ratio of thickness of each member or the like are different from the actual relationship, ratio or the like, and it goes without saying that parts are included which have dimensional relationships and ratios differing among the drawings.

First Embodiment

Figure 1:
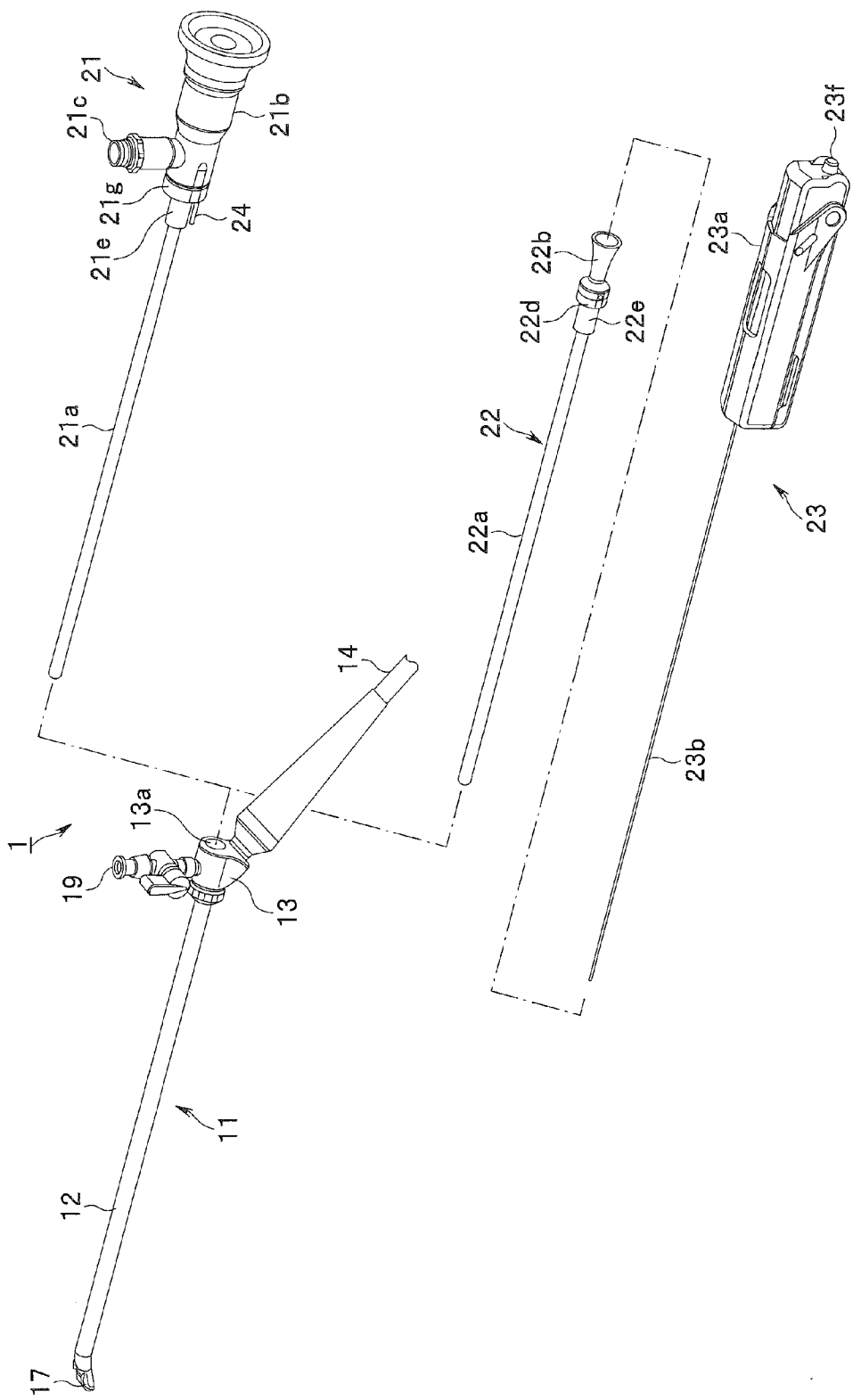
FIG. 1 is a perspective view of a rigid endoscope set according to a first embodiment.

FIG. 1 to FIG. 10 illustrate a first embodiment of the present invention. FIG. 1 shows a configuration of a rigid endoscope set. The rigid endoscope set 1 includes a rigid endoscope body 11, an optical telescope 21 as an imaging device, a treatment instrument guide 22 and a treatment instrument apparatus 23. The rigid endoscope set 1 of the present embodiment is used to transurethrally extract a living tissue of the prostate gland, for example.

The rigid endoscope body 11 includes a first insertion portion 12 which is inserted into a luminal (e.g., urethra) of a subject, a grasping portion 13 is provided on the user's hand side of the first insertion portion 12 and a universal cord 14 extends from one side of the grasping portion 13. The first insertion portion 12 is rigid and extends rectilinearly, and a signal cable 15 that extends from the universal cord 14 is inserted along an axial direction on a lower side in the first insertion portion 12. Furthermore, a first channel 16 is formed along an axial direction on an upper side in the first insertion portion 12 and a front end of the first channel 16 is open to a front end face of the first insertion portion 12. Note that an inner diameter of the first channel 16 is set to a size which is adapted to an outer diameter of a third insertion portion 21a provided in the optical telescope 21, which will be described later.

Figure 10:
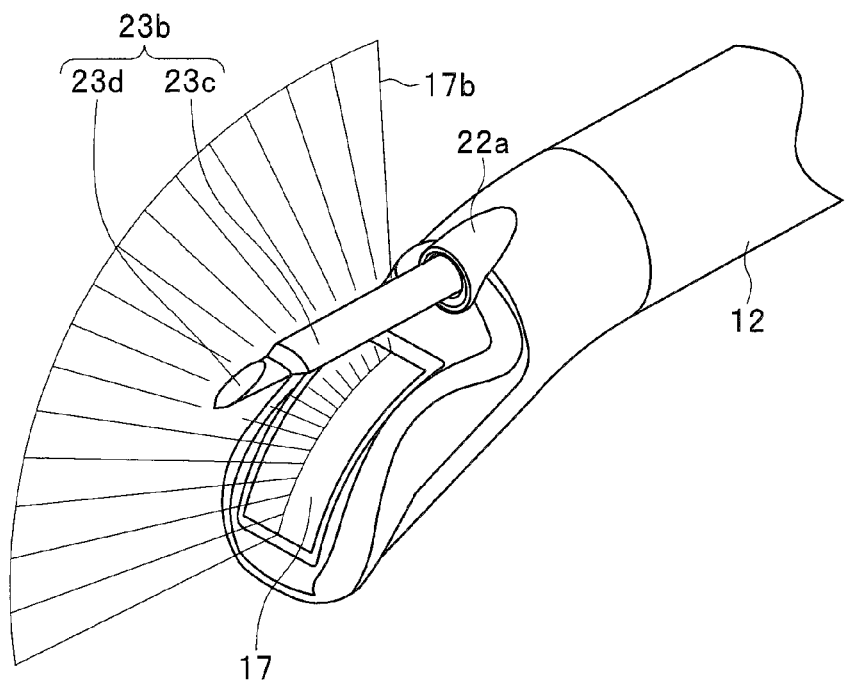
FIG. 10 is a perspective view of the distal end portion from which the treatment instrument protrudes via the treatment instrument guide from the distal end of the rigid endoscope body according to the first embodiment.

A first observation section 17 to observe the subject is provided at a distal end of the first insertion portion 12. The first observation section 17 is provided with an ultrasound observation section 17a composed of a convex array type ultrasound transducer and a distal end portion of the signal cable 15 is connected to the ultrasound observation section 17a. Furthermore, as shown in FIG. 10, the ultrasound observation section 17a is arranged so as to cause the ultrasound transducer to follow an axis center of the first insertion portion 12 and to scan an extension of an axis of the first channel 16 in a fan shape.

Note that although not shown, a connector is provided at a proximal end of the universal cord 14 and the connector is connected to a signal processing unit. The signal processing unit transmits a drive signal to the ultrasound observation section 17a via the signal cable 15, processes an ultrasound signal received by the ultrasound observation section 17a, generates an ultrasound image of a tissue located closer in a depth direction than a body cavity wall of the subject and causes a monitor (not shown) to display the ultrasound image.

A water supply port 19 with a cock is provided at a top of the grasping portion 13. The water supply port 19 is configured to be open inside the first channel 16 and to freely supply a perfusate via a perfusion tube (not shown). An operator opens the cock of the water supply port 19, and can thereby supply the perfusate into the first channel 16 as appropriate.

Figure 7:
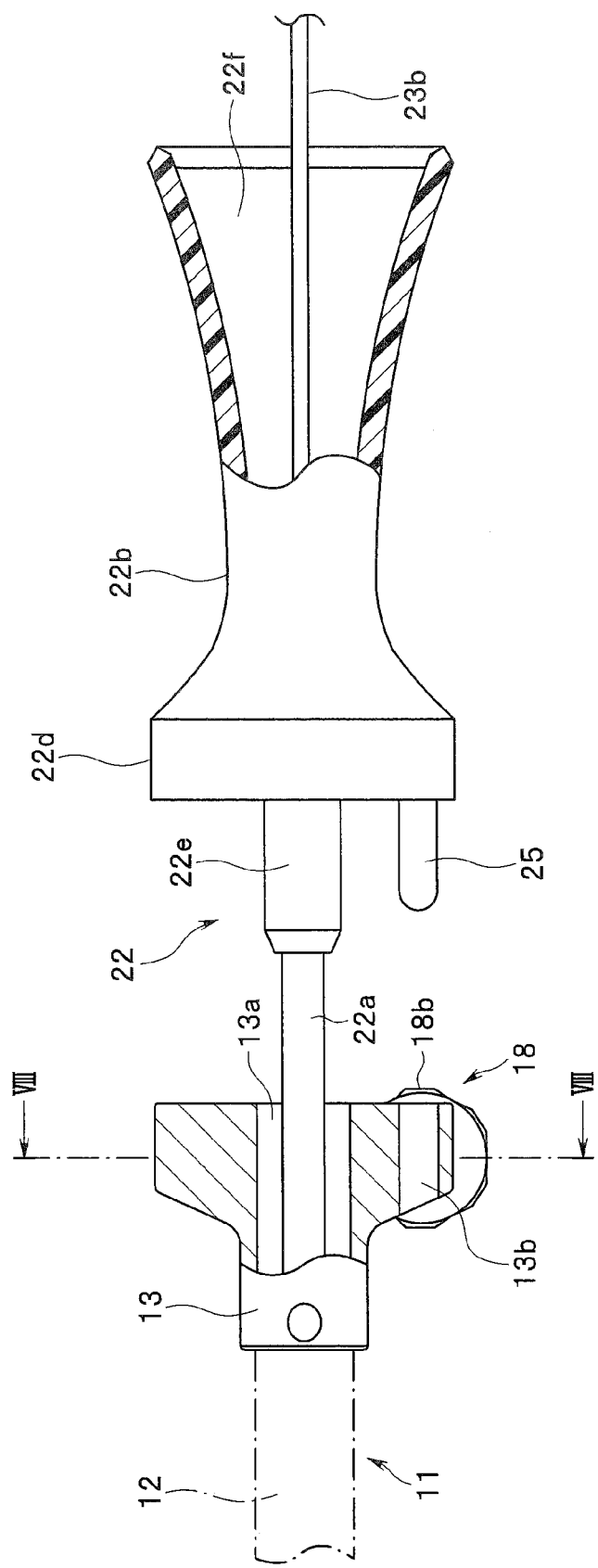
FIG. 7 is a partial cross-sectional side view illustrating the treatment instrument guide into/from which the treatment instrument is inserted/removed being positioned at a proximal end portion of the rigid endoscope body according to the first embodiment.
Figure 8:
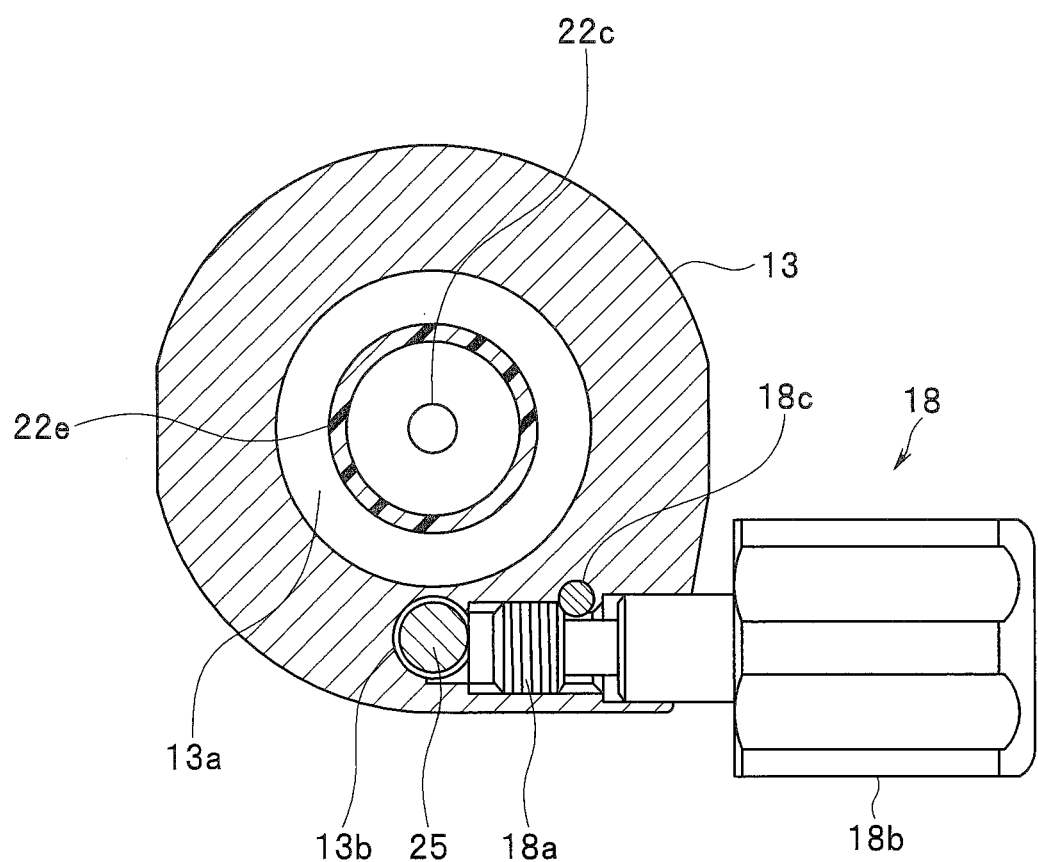
FIG. 8 is a VIII-VIII cross-sectional view in FIG. 7 according to the first embodiment.

Furthermore, as shown in FIG. 7, an insertion guide hole 13a that communicates with the first channel 16 is formed in the grasping portion 13 and a rear end of the insertion guide hole 13a is open to a rear end face of the grasping portion 13. A positioning hole 13b is drilled in the rear end face of the grasping portion 13. Positioning pins 24 and 25 provided so as to protrude from the optical telescope 21 and the treatment instrument guide 22, which will be described later, are engageably inserted into the positioning hole 13b. Furthermore, as shown in FIG. 8, the grasping portion 13 is provided with a fixing screw 18. The fixing screw 18 includes a threaded portion 18a configured to press the positioning pins 24 and 25 against one side of the positioning hole 13b, a turning knob 18b is fixed to the threaded portion 18a so as to be grasped and turned by the operator and the threaded portion 18a is prevented from falling out by a retaining pin 18c.

The third insertion portion 21a provided in the optical telescope 21 or the second insertion portion 22a provided in the treatment instrument guide 22 is selectively inserted into or removed from the first channel 16 of the rigid endoscope body 11. Both insertion portions 21a and 22a are rigid and extend rectilinearly, and the inner diameter of the first channel 16 is set to such a size that is adapted to the outer diameter of the third insertion portion 21a. On the other hand, the outer diameter of the second insertion portion 22a is set to be identical to the outer diameter of the third insertion portion 21a. Although not shown in FIG. 4 and FIG. 9, a minute gap that allows the perfusate to circulate is secured between an inner circumference of the first channel 16 and outer circumferences of both insertion portions 21a and 22a. Therefore, the inner diameter of the first channel 16 is set to be slightly greater than the outer diameters of both insertion portions 21a and 22a by the size of the gap that allows the perfusate to circulate.

Furthermore, as shown in FIG. 1, an eyepiece section 21b is provided on the user's hand side of the third insertion portion 21a provided in the optical telescope 21 and a pipe sleeve portion 21c into which a light guide (not shown) is inserted and connected is provided at a top near a front end of the eyepiece section 21b. The light guide passes through the third insertion portion 21a and extends toward the distal end direction, and illuminating light transmitted through the light guide is emitted from an illuminating window (not shown) provided at a distal end portion of the third insertion portion 21a and radiated onto a body cavity wall of the subject. An observation window (hereinafter referred to as "second observation section") 21d is provided at a distal end of the third insertion portion 21a adjacent to the illuminating window, reflected light from the body cavity wall of an object enters the second observation section 21d, and an object image formed in an optical observation section 21f provided inside the second observation section 21d is transmitted to the eyepiece section 21b via a relay optical system and observed.

Furthermore, a flange portion 21g is formed at a front end of the eyepiece section 21b. A support portion 21e is provided so as to protrude from the center of a front end face of the flange portion 21g and a rear end of the third insertion portion 21a is supported by the support portion 21e. A front end face of the flange portion 21g is disposed so as to face a rear end face of the grasping portion 13 provided in the rigid endoscope body 11 and the support portion 21e is inserted through an insertion guide hole 13a which is open to the rear end face of the grasping portion 13. The positioning pin 24 (see FIG. 1) is provided so as to protrude at a lower part of the front end face of the flange portion 21g. The positioning pin 24 is engageably inserted into the positioning hole 13b which is open to the rear end face of the grasping portion 13 and movement in a turning direction is thereby restricted.

On the other hand, a funnel-shaped guidance portion 22b is provided on the user's hand side of the second insertion portion 22a provided in the treatment instrument guide 22. Furthermore, a flange portion 22d is formed at a distal end of the guidance portion 22b, a support portion 22e is provided so as to protrude at the center of a front end face of the flange portion 22d and a rear end of the second insertion portion 22a is supported by the support portion 22e. The front end face of the flange portion 22d is disposed so as to face the rear end face of the grasping portion 13 provided in the rigid endoscope body 11 and the support portion 22e is inserted through the insertion guide hole 13a which is open to the rear end face of the grasping portion 13. Furthermore, the positioning pin 25 is provided so as to protrude from a lower part of the front end face of the flange portion 22d. The positioning pin 25 is engageably inserted into the positioning hole 13b which is open to the rear end face of the grasping portion 13 and movement in a turning direction is thereby restricted.

A second channel 22c is formed in an axis center in the second insertion portion 22a of the treatment instrument guide 22 and a front end of the second channel 22c is open to a front end face of the second insertion portion 22a. Furthermore, a rear end of the second channel 22c communicates with a guidance hole 22f formed in the guidance portion 22b. An elongated rigid treatment instrument 23b which rectilinearly extends forward from an apparatus body 23a provided in the treatment instrument apparatus 23 is inserted into or removed from the second channel 22c.

The second channel 22c is intended to function as a guide when the treatment instrument 23b is inserted or removed and an inner diameter of the second channel 22c is formed to be slightly greater than an outer diameter of the treatment instrument 23b. Note that in the present embodiment, the second insertion portion 22a is formed of a pipe material, an interior of the second insertion portion 22a is filled with a resin material and the second channel 22c is formed in the filling resin material. Note that the second insertion portion 22a may be made of a solid metal and the second channel 22c may be formed in the metal.

In the present embodiment, a biopsy apparatus is shown as an example of the treatment instrument apparatus 23 and a needle portion of the biopsy apparatus corresponds to the treatment instrument 23b. Therefore, the description will be given hereinafter by reading the treatment instrument apparatus 23 as a biopsy apparatus 23 and the treatment instrument 23b as a needle portion 23b.

The needle portion 23b includes a guide barrel needle 23c having a smaller outer diameter than that of the third insertion portion 21a of the optical telescope 21 and a biopsy needle 23d, and the biopsy needle 23d is inserted through the guide barrel needle 23c so as to freely advance and retract. A pocket 23e is formed on a distal end side of the biopsy needle 23d. When an ejection button 23f provided on a rear face of the apparatus body 23a is pressed, the biopsy needle 23d projects forward by a spring force of a spring provided in the apparatus body 23a, is punctured into a tissue of the subject and the living tissue is taken into the pocket 23e. When the ejection button 23f is pressed, the guide barrel needle 23c projects following the biopsy needle 23d and when a distal end of the guide barrel needle 23c passes over the pocket 23e, the living tissue is extracted and taken into the pocket 23e.

As shown in FIG. 10, since the axis center of the first channel 16 is disposed at a position where it protrudes toward a scanning surface (observation view field) 17b of the ultrasound observation section 17a, if the needle portion 23b is caused to protrude forward from the axis center of the first channel 16, the needle portion 23b penetrates the scanning surface 17b of the ultrasound observation section 17a, and therefore the needle portion 23b can be displayed on an ultrasound image on a monitor.

The needle portion 23b of the present embodiment is inserted through the first channel 16 via the second insertion portion 22a provided in the treatment instrument guide 22. Therefore, if the outer diameter of the second insertion portion 22a is set in correspondence with the inner diameter of the first channel 16 and the inner diameter of the second channel 22c formed in the second insertion portion 22a is set in correspondence with the outer diameter of the needle portion 23b, the needle portion 23b which is thinner than the third insertion portion 21a of the telescope 21 can accurately project toward the scanning surface 17b of the ultrasound observation section 17a.

Figure 2:
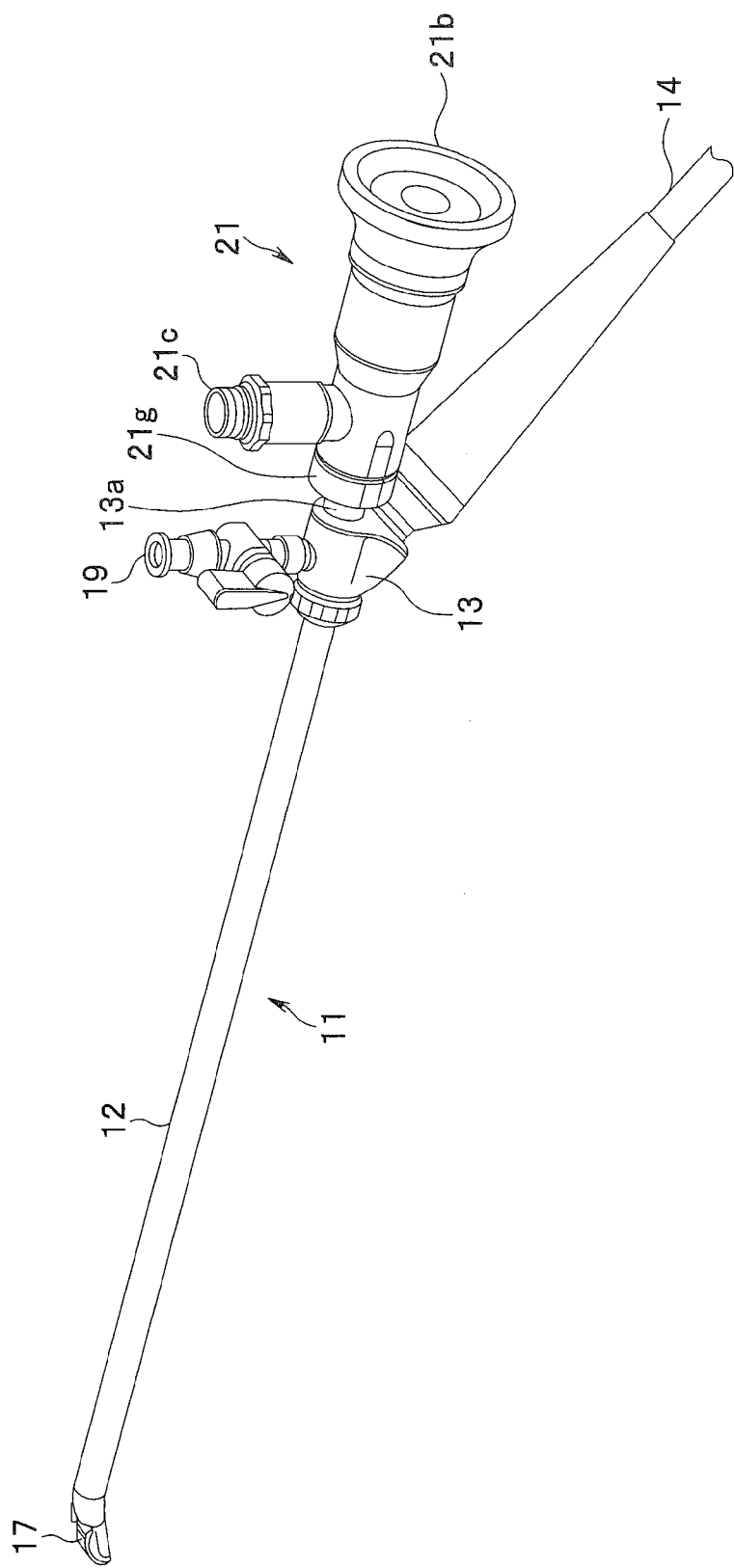
FIG. 2 is a perspective view illustrating an optical telescope inserted into a rigid endoscope body according to the first embodiment.

Next, operation of extracting a living tissue using the rigid endoscope set 1 having such a configuration will be described. When the rigid endoscope body 11 is inserted into the subject and the first observation section 17 provided at the distal end portion is guided to a target body cavity wall, as shown in FIG. 2, the third insertion portion 21a of the optical telescope 21 is inserted into the first channel 16 formed in the first insertion portion 12 of the rigid endoscope body 11 from the insertion guide hole 13a which is open to the rear end face of the grasping portion 13.

Figure 3:
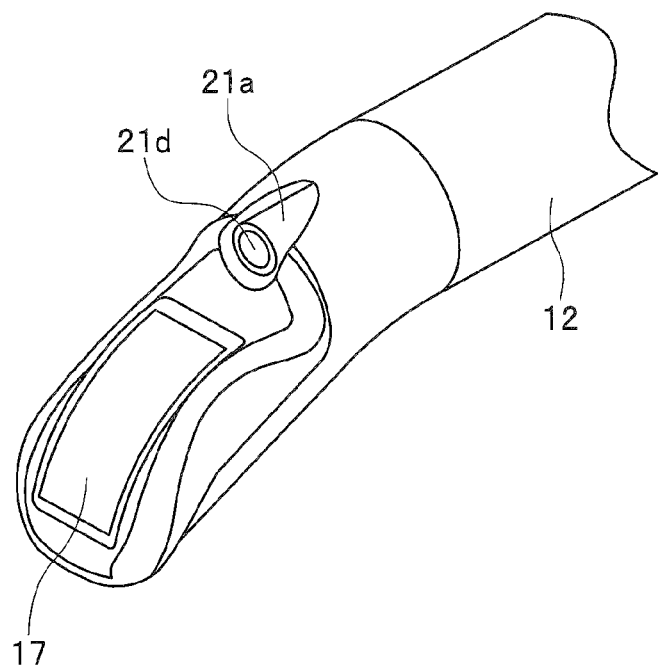
FIG. 3 is a perspective view of a distal end portion of the rigid endoscope body according to the first embodiment.
Figure 4:
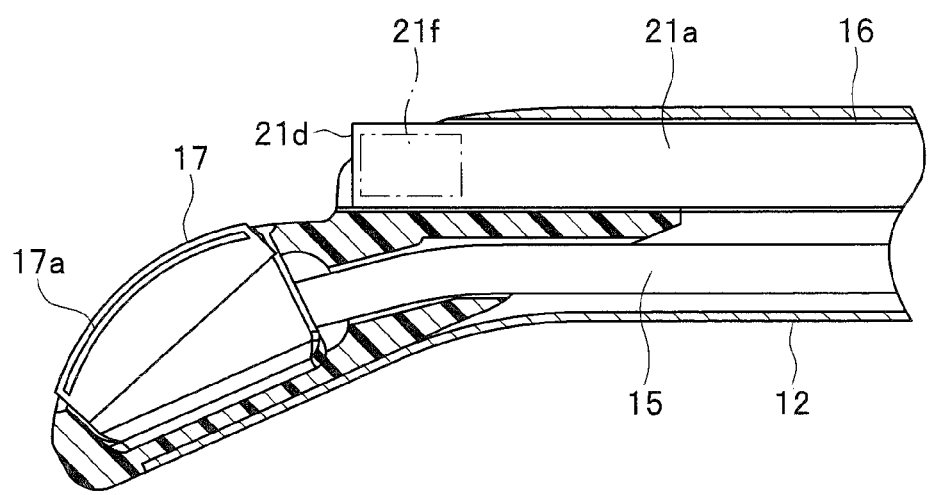
FIG. 4 is a side cross-sectional view of the distal end portion in FIG. 1 of the rigid endoscope set according to the first embodiment.

As shown in FIG. 3 and FIG. 4, the distal end of the third insertion portion 21a projects from the opening of the first channel 16 which is open at the distal end of the first insertion portion 12, and the positioning pin 24 (see FIG. 1) that protrudes on the front end face of the flange portion 21g of the eyepiece section 21b provided on the user's hand side is engageably inserted into the positioning hole 13b drilled in the rear end face of the grasping portion 13 provided in the rigid endoscope body 11 and the third insertion portion 21a is positioned in the first channel 16 of the rigid endoscope body 11. After that, the threaded portion 18a is turned via the turning knob 18b of the fixing screw 18 provided in the grasping portion 13 and the positioning pin 24 engageably inserted into the positioning hole 13b is pressed by the distal end against the inner wall on the opposite side and fixed.

Next, the first insertion portion 12 of the rigid endoscope body 11 to which the optical telescope 21 is fixed is inserted into the luminal (e.g., urethra) of the subject and the first observation section 17 provided at the distal end is guided to a target region (e.g., urethra in the prostate gland) while checking the endoscope image in the subject imaged in the eyepiece section 21b. When the first observation section 17 reaches the target region, the fixing screw 18 is loosened while retaining the rigid endoscope body 11 in the body cavity of the subject and the third insertion portion 21a of the optical telescope 21 is removed from the first channel 16.

Figure 6:
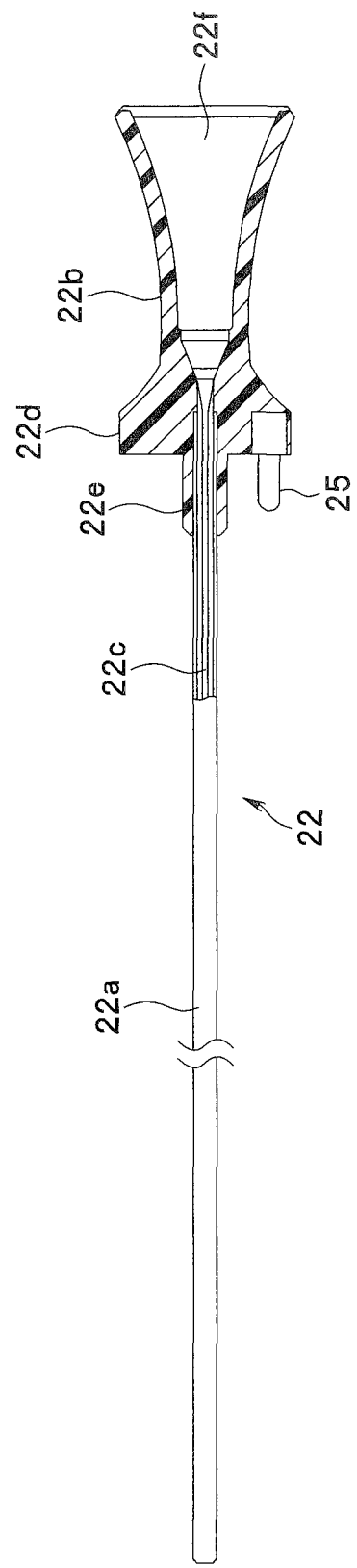
FIG. 6 is a side cross-sectional view of the treatment instrument guide according to the first embodiment.
Figure 9:
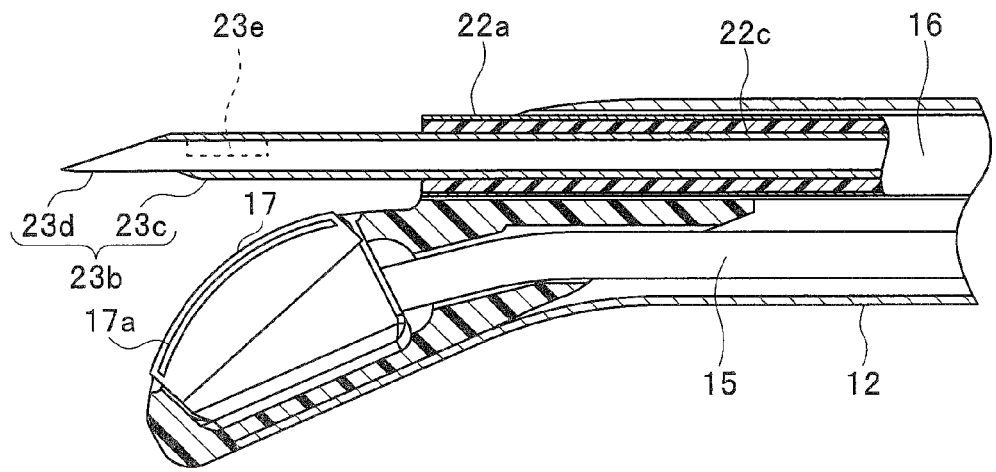
FIG. 9 is a cross-sectional side view of the distal end portion from which the treatment instrument protrudes via the treatment instrument guide from the distal end of the rigid endoscope body according to the first embodiment.

After that, the second insertion portion 22a of the treatment instrument guide 22 shown in FIG. 6 is inserted into the first channel 16, and as shown in FIG. 7, the positioning pin 25 that protrudes from the front end face of the flange portion 22d on the user's hand side is engageably inserted into the positioning hole 13b drilled in the grasping portion 13 provided on the user's hand side of the rigid endoscope body 11, and as shown in FIG. 8, the positioning pin 25 is pressed against the inner wall of the positioning hole 13b on the opposite side and fixed using the fixing screw 18. Then, as shown in FIG. 9, the distal end of the second insertion portion 22a is located at substantially the same position as the opening of the first channel 16. Since the gap between the outer diameter of the second insertion portion 22a and the inner diameter of the first channel 16 is minute, no backlash occurs in the diameter direction and the axis center of the second insertion portion 22a substantially coincides with the axis of the first channel 16 and is fixed.

Figure 5:
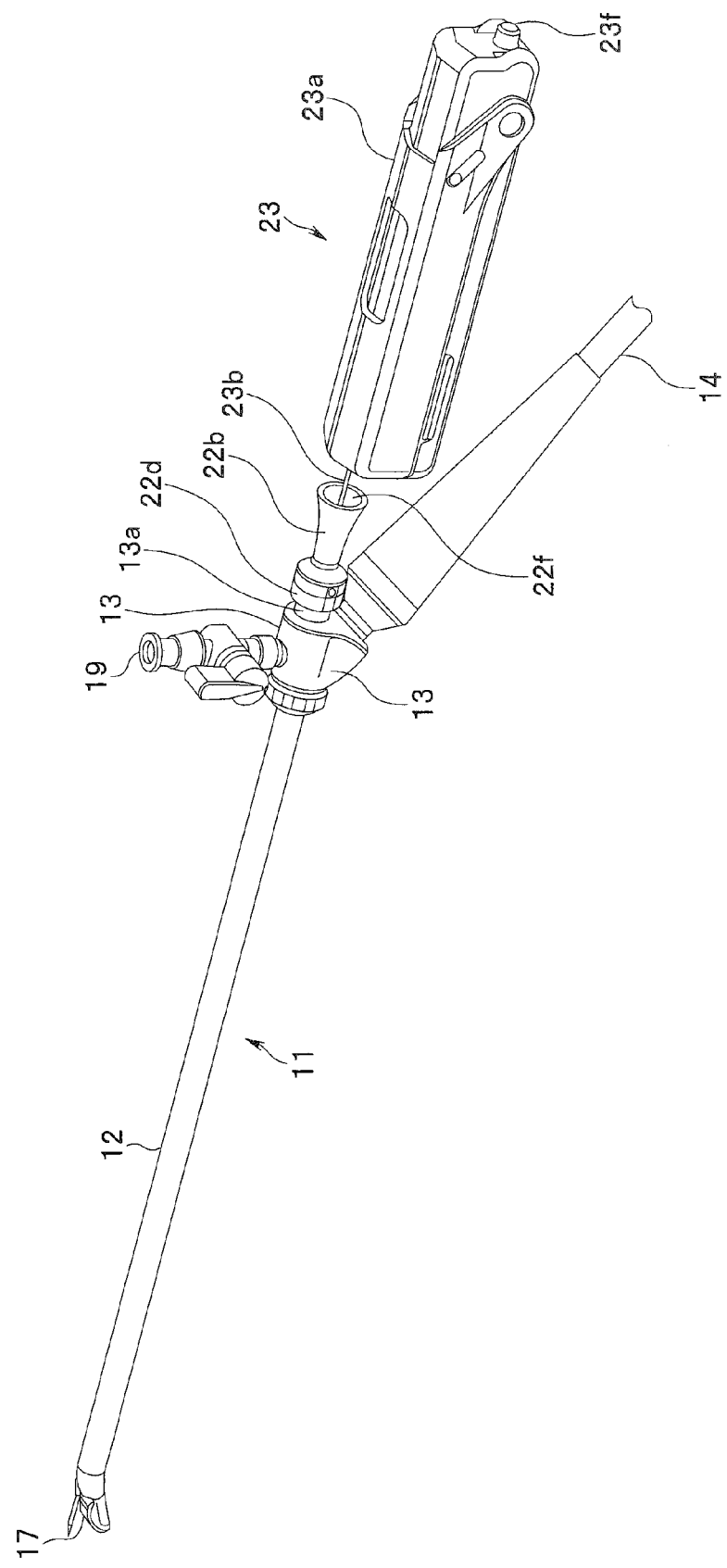
FIG. 5 is a perspective view illustrating a treatment instrument being inserted into the rigid endoscope body via a treatment instrument guide according to the first embodiment.

After that, the needle portion 23b provided in the biopsy apparatus 23 is inserted into the second channel 22c from the guidance hole 22f formed in the guidance portion 22b, and as shown in FIG. 5 and FIG. 9, the distal end of the needle portion 23b projects from the opening at the distal end of the second channel 22c. Since the gap between the inner diameter of the second channel 22c and the outer diameter of the needle portion 23b is minute, substantially no backlash occurs in the diameter direction, and the axis center of the needle portion 23b substantially coincides with the axis center of the first channel 16 and is held so as to freely advance and retract.

Therefore, as shown in FIG. 10, the distal end of the needle portion 23b projects in the direction penetrating the scanning surface 17b of the first observation section 17. As a result, the distal end of the needle portion 23b is displayed on an ultrasound image on the monitor, and so, the operator checks the distal end of the needle portion 23b imaged on the monitor, presses the ejection button 23f provided in the apparatus body 23a, and can thereby easily extract a living tissue at an optimum position.

Thus, according to the present embodiment, the outer diameter of the second insertion portion 22a provided in the treatment instrument guide 22 is formed to be identical to the outer diameter of the third insertion portion 21a provided in the telescope 21 and the inner diameter of the second channel 22c formed in the second insertion portion 22a is formed so as to be adapted to the needle portion 23b of the biopsy apparatus 23, and therefore the needle portion 23b provided in the biopsy apparatus 23 is inserted into the first channel 16 of the rigid endoscope body 11 via the second insertion portion 22a of the treatment instrument guide 22, and it is thereby possible to accurately guide the distal end of the needle portion 23b to the body cavity wall of the subject without producing backlash in the needle portion 23b through the operation on the user's hand side.

Furthermore, since the axis center of the needle portion 23b coincides with the scanning surface 17b of the first observation section 17, it is possible to display the needle portion 23b on the ultrasound image on the monitor and the operator can thereby guide the needle portion 23b to an optimum position while checking the needle portion 23b using the monitor.

Second Embodiment

Figure 11:
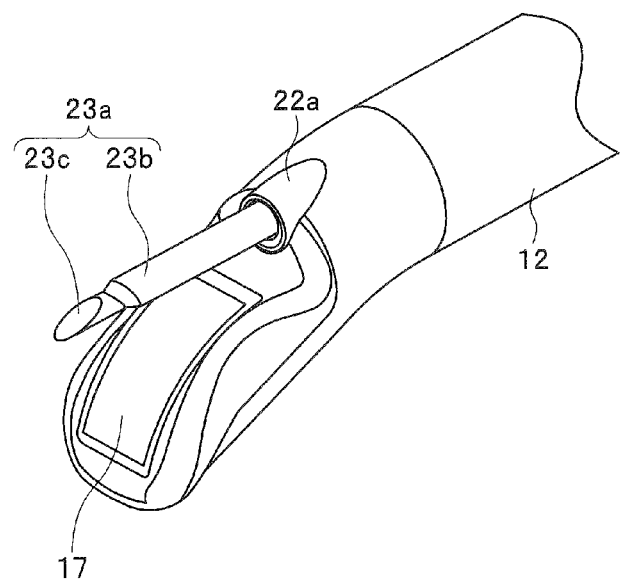
FIG. 11 is a perspective view of a distal end portion from which a treatment instrument protrudes via a treatment instrument guide from a distal end of a rigid endoscope body according to a second embodiment.
Figure 12:
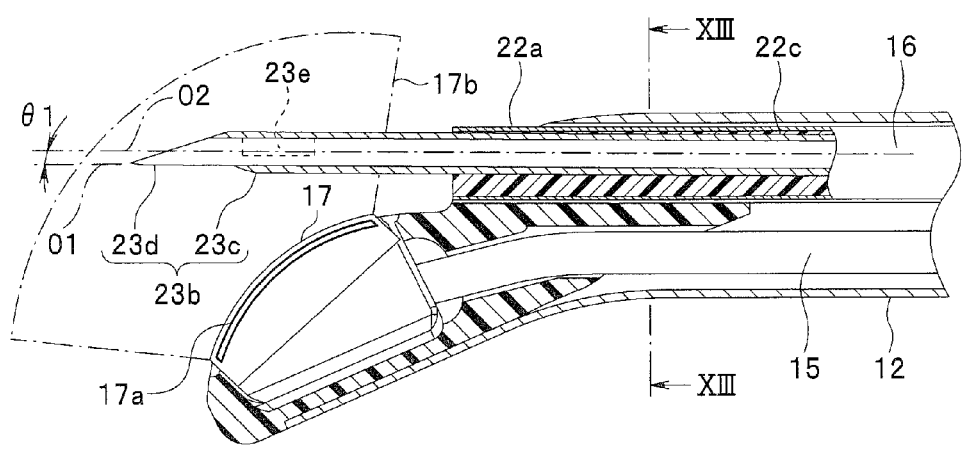
FIG. 12 is a cross-sectional side view of the distal end portion illustrating the treatment instrument protruding via the treatment instrument guide from the distal end of the rigid endoscope body according to the second embodiment.
Figure 13:
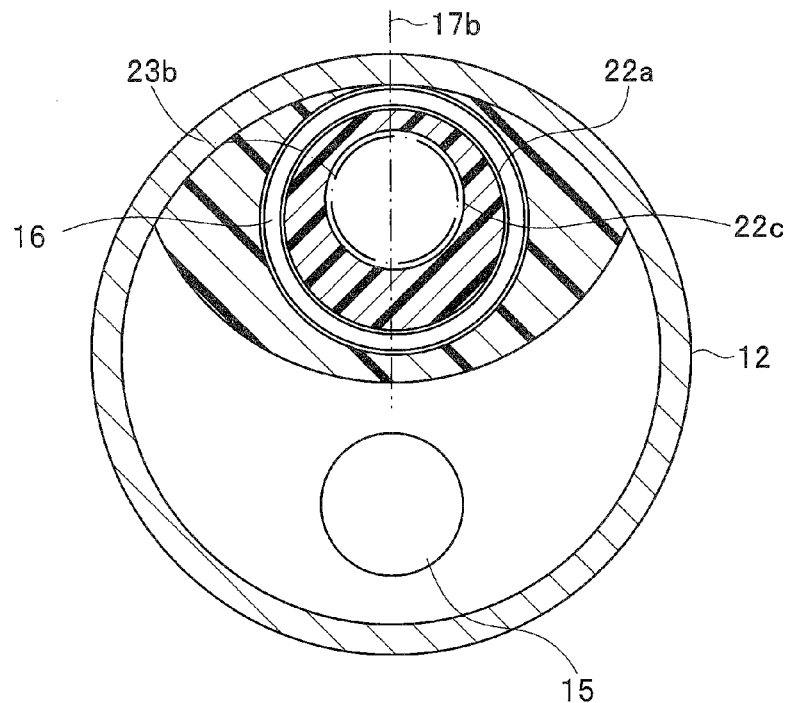
FIG. 13 is a XIII-XIII cross-sectional view in FIG. 12 of the rigid endoscope set according to the second embodiment.

FIG. 11 to FIG. 13 show a second embodiment of the present invention. In the first embodiment, the axis center of the first channel 16 provided in the rigid endoscope body 11 is made to coincide with the axis center of the second channel 22c provided in the treatment instrument guide 22, whereas in the present embodiment, the axis center of the second channel 22c is caused to incline upward (direction departing from the first observation section) as the axis center moves toward the distal end direction so that the axis center of the second channel 22c is decentered from the axis center of the second insertion portion 22a. Therefore, the amount of decentering of the second channel 22c from the axis center of the second insertion portion 22a differs between the distal end side and the user's hand side, and the amount of decentering gradually increases from the user's hand side to the distal end side. Note that components identical to those of the first embodiment are assigned identical reference numerals and description will be omitted.

That is, as shown in FIG. 12, an axis center O2 of the second channel 22c provided in the treatment instrument guide 22 is caused to incline upward by a predetermined angle of inclination θ1 with respect to an axis center O1 of the first channel 16 which is parallel to the axis center of the first insertion portion 12. On the other hand, the axis center of the guidance hole 22f drilled in the guidance portion 22b provided on the user's hand side of the treatment instrument guide 22 crosses the axis center of the second insertion portion 22a in the vicinity of a joint between the guidance portion 22b and the second insertion portion 22a.

Therefore, as shown in FIG. 13, the distal end of the second channel 22c is open at a position decentered upward by a predetermined amount along the scanning surface 17b of the first observation section 17 from the axis center of the treatment instrument guide 22, and therefore the needle portion 23b of the biopsy apparatus 23 inserted through the second channel 22c protrudes diagonally upward from the distal end of the second channel 22c. As shown in FIG. 12, by causing the needle portion 23b to project diagonally upward, the distance between the distal end of the needle portion 23b and the first observation section 17 increases compared to that in the first embodiment, and it is therefore possible to display the needle portion 23b longer with respect to the ultrasound image displayed in a fan shape on the monitor.

Third Embodiment

Figure 14:
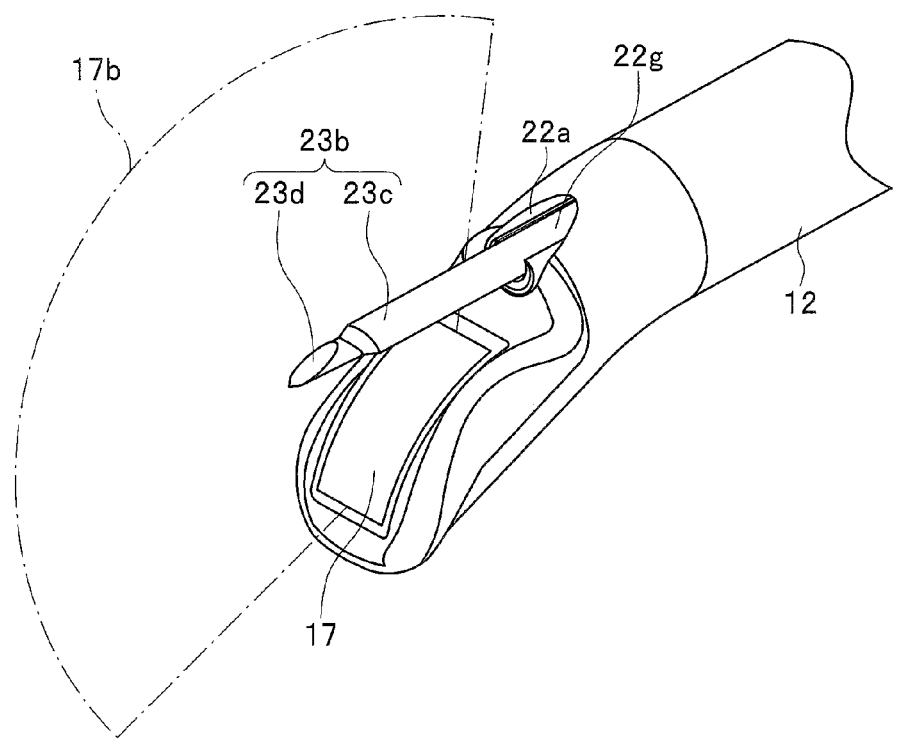
FIG. 14 is a perspective view of a distal end portion illustrating a treatment instrument protruding via a treatment instrument guide from a distal end of a rigid endoscope body according to a third embodiment.
Figure 15:
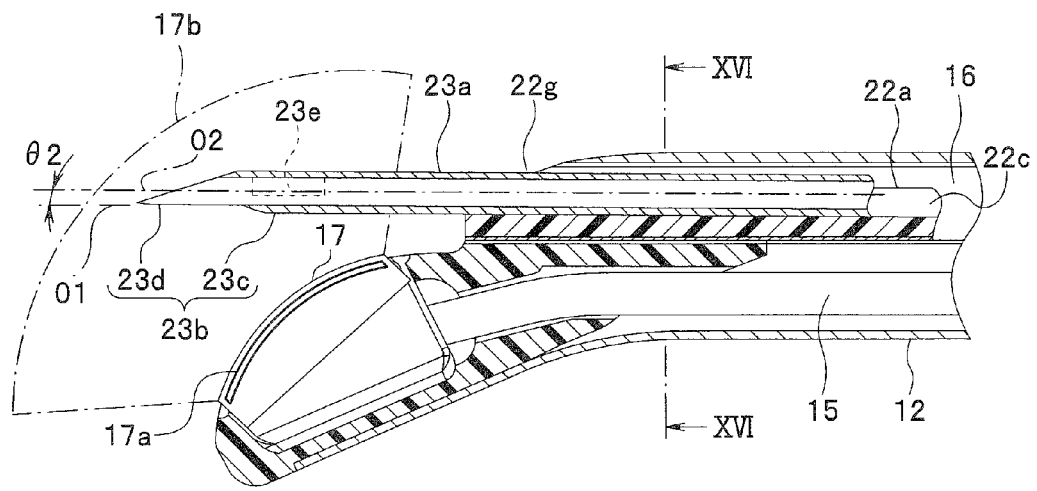
FIG. 15 is a cross-sectional side view of the distal end portion illustrating the treatment instrument protruding via the treatment instrument guide from the distal end of the rigid endoscope body according to the third embodiment.
Figure 16:
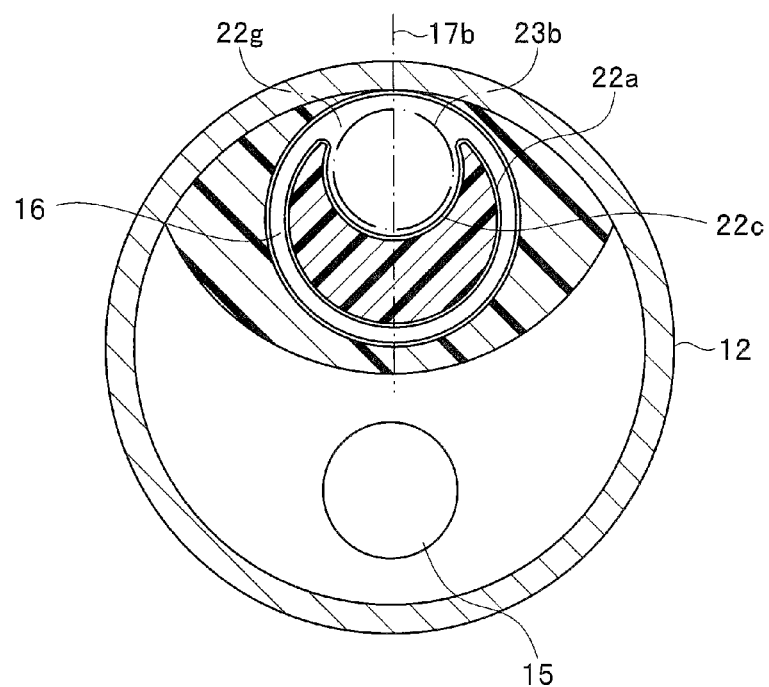
FIG. 16 is a XVI-XVI cross-sectional view in FIG. 15 of the rigid endoscope body according to the third embodiment.

FIG. 14 to FIG. 16 illustrate a third embodiment of the present invention. An opening 22g is formed along the axial direction at a top of the second channel 22c provided in the treatment instrument guide 22 of the present embodiment. If the width of the opening 22g in the diameter direction is narrower than the diameter of the needle portion 23b, the needle portion 23b never goes out from the opening 22g and is held in the second channel 22c so as to freely advance and retract with the movement in the diameter direction being restricted.

On the other hand, by forming the opening 22g at the top of the second channel 22c, the needle portion 23b can be caused to incline further upward on the distal end side of the second channel 22c as shown in FIG. 16. For this reason, as shown in FIG. 15, an angle of inclination θ2 of the needle portion 23b is greater than in the case of the second embodiment, and the distal end of the second channel 22c can be made open at a position more decentered upward along the scanning surface 17b of the first observation section 17 from the axis center of the treatment instrument guide 22 than the case of the second embodiment.

As a result, according to the present embodiment, the distance between the distal end of the needle portion 23b and the first observation section 17 increases compared to that in the case of the second embodiment, and the needle portion 23b can be displayed longer accordingly with respect to the ultrasound image on the monitor.

Note that the present invention is not limited to the aforementioned embodiments. For example, the treatment instrument apparatus is not limited to the biopsy apparatus 23, but may also be an injection needle, high-frequency knife or the like as long as such a device is provided with a treatment instrument having an outer diameter smaller than that of the third insertion portion 21a of the optical telescope 21. Regarding the direction of inclination of the second channel 22c, the second channel 22c may be caused to incline downward (in the direction approaching the first observation section 17) so that the treatment instrument may puncture at a shallower position or may only be decentered while keeping the second channel 22c parallel to the axis center of the first channel 16.

What is claimed is:

1. A rigid endoscope set comprising:
   a rigid endoscope body comprising a first insertion portion inserted into a subject configured to include an elongated longitudinal axis, a first channel provided in the first insertion portion and an ultrasound observation section disposed at a distal end of the first insertion portion to observe the subject;
   a treatment instrument guide comprising a second insertion portion configured to be insertable into or removable from the first channel and formed to have an outer diameter adaptable to the first channel and a second channel formed of a resin material filling an interior of the second insertion portion such that an axis of the second channel is inclined from a user's hand side with respect to an axis center of the second insertion portion;
   a treatment instrument insertable into or removable from the second channel;
   an imaging device comprising a third insertion portion formed to be insertable into or removable from the first channel instead of the treatment instrument guide with an outer diameter adaptable to the first channel and an optical observation section disposed at a distal end of the third insertion portion to observe the subject; and
   a positioning mechanism configured to fix, when the imaging device is inserted into the first channel, the rigid endoscope body and the imaging device in a state in which a minute gap is secured to circulate a perfusate between the first channel and the third insertion portion, fix the imaging device to restrict the imaging device from moving in a turning direction of the longitudinal axis of the rigid endoscope body, and fix, when the treatment instrument guide is inserted into the first channel, the treatment instrument guide to the rigid endoscope body and fix the treatment instrument guide to restrict the treatment instrument guide from moving in the turning direction of the longitudinal axis of the rigid endoscope body,
   wherein, in a state in which the treatment instrument guide is fixed to the rigid endoscope body, the inclination of the axis center of the second channel causes the second channel to open at a position where the axis center of the second channel is decentered in a direction in which the axis center of the second channel moves away from the ultrasound observation section with respect to the axis center of the first channel and the treatment instrument projects in a direction in which the treatment instrument moves away from the ultrasound observation section.

2. The rigid endoscope set according to claim 1, wherein the first channel is disposed at a position at which the treatment instrument projects in a field of view of observation by the ultrasound observation section.

3. The rigid endoscope set according to claim 2, wherein the second channel comprises an opening formed along the direction of the longitudinal axis on a side face of the second insertion portion, and a width of the opening in a diameter direction is narrower than a diameter of the treatment instrument.

4. The rigid endoscope set according to claim 1, wherein the positioning mechanism fixes the rigid endoscope body and the treatment instrument guide in a state in which a minute gap is secured to circulate a perfusate between the first channel and the second insertion portion.

5. The rigid endoscope set according to claim 1, wherein the positioning mechanism comprises a positioning hole provided in the rigid endoscope body along an axis direction of the rigid endoscopy body and a positioning pin provided in the imaging device and configured to be engageably inserted into the positioning hole.

6. The rigid endoscope set according to claim 1, wherein the positioning mechanism fixes the rigid endoscope body and the imaging device by fixing the positioning pin engageably inserted into the positioning hole using a fixing screw.

7. The rigid endoscope set according to claim 1, wherein an axis center of the first insertion portion and the axis center of the first channel are parallel to each other.

8. The rigid endoscope set according to claim 1, wherein the positioning mechanism positions the distal end of the third insertion portion at a position where the distal end projects from an opening of the first channel which is open at the distal end of the first insertion portion.

9. The rigid endoscope set according to claim 1, wherein the second insertion portion of the treatment instrument guide is rigid and extends rectilinearly.

10. The rigid endoscope set according to claim 1, wherein the third insertion portion of the imaging device is rigid and extends rectilinearly.

11. The rigid endoscope set according to claim 1, wherein the axis center of the first channel of the rigid endoscope body and the axis center of the second channel of the treatment instrument guide are decentered while being kept parallel to each other.

* * * * *